United States Patent
Pue

Patent Number: 5,000,175
Date of Patent: Mar. 19, 1991

[54] MECONIUM ASPIRATION DEVICE

[76] Inventor: Alexander F. Pue, 3652 Carleton St., San Diego, Calif. 92106

[21] Appl. No.: 390,926

[22] Filed: Aug. 8, 1979

[51] Int. Cl.$^5$ .............................................. A61M 16/00
[52] U.S. Cl. ........................... 128/207.14; 128/207.16; 128/912; 604/119
[58] Field of Search .................... 128/911, 912, 207.14, 128/207.16, 200.24, 200.26, 202.27, DIG. 26, 204.18; 604/35, 119, 100

[56] References Cited

U.S. PATENT DOCUMENTS

| | | | |
|---|---|---|---|
| 3,893,446 | 7/1975 | Miller | 128/DIG. 26 |
| 3,958,566 | 5/1976 | Furihata | 604/35 |
| 4,198,958 | 4/1980 | Utsugi | 604/119 |
| 4,248,236 | 2/1981 | Linder | 604/100 |
| 4,291,691 | 9/1981 | Cabal et al. | 128/912 |
| 4,530,354 | 7/1985 | Froilan | 128/207.17 |
| 4,699,138 | 10/1987 | Behrstock | 604/119 |
| 4,821,714 | 4/1989 | Smelser | 128/207.14 |
| 4,850,984 | 7/1989 | Harris | 128/912 |

*Primary Examiner*—Edgar S. Burr
*Assistant Examiner*—Stephen R. Funk
*Attorney, Agent, or Firm*—Albert O. Cota

[57] ABSTRACT

A meconium aspiration device which has a body (20) with a hollow chamber (26) inside. One end has an inlet opening (22) to which a suction catheter (30) is attached and the other end has a finger control port (24) with a groove (38) on the side. An outlet passage (28) at 45 degrees to the inlet opening has a tube (40) attached to a suction source and a stylet (34) is placed within the port, chamber and catheter allowing the catheter to be pre-shaped for intubation into a newborn. For meconium removal, the catheter is intubated and one's finger is placed over the port to control suction with the stylet retained in place or removed, as desired. Ventilation may be accomplished with the device by fixing a common ventilation mechanism over the finger control port with the stylet removed while on occlusion slide on the suction tube is used to pinch off communication with the suction source.

8 Claims, 2 Drawing Sheets

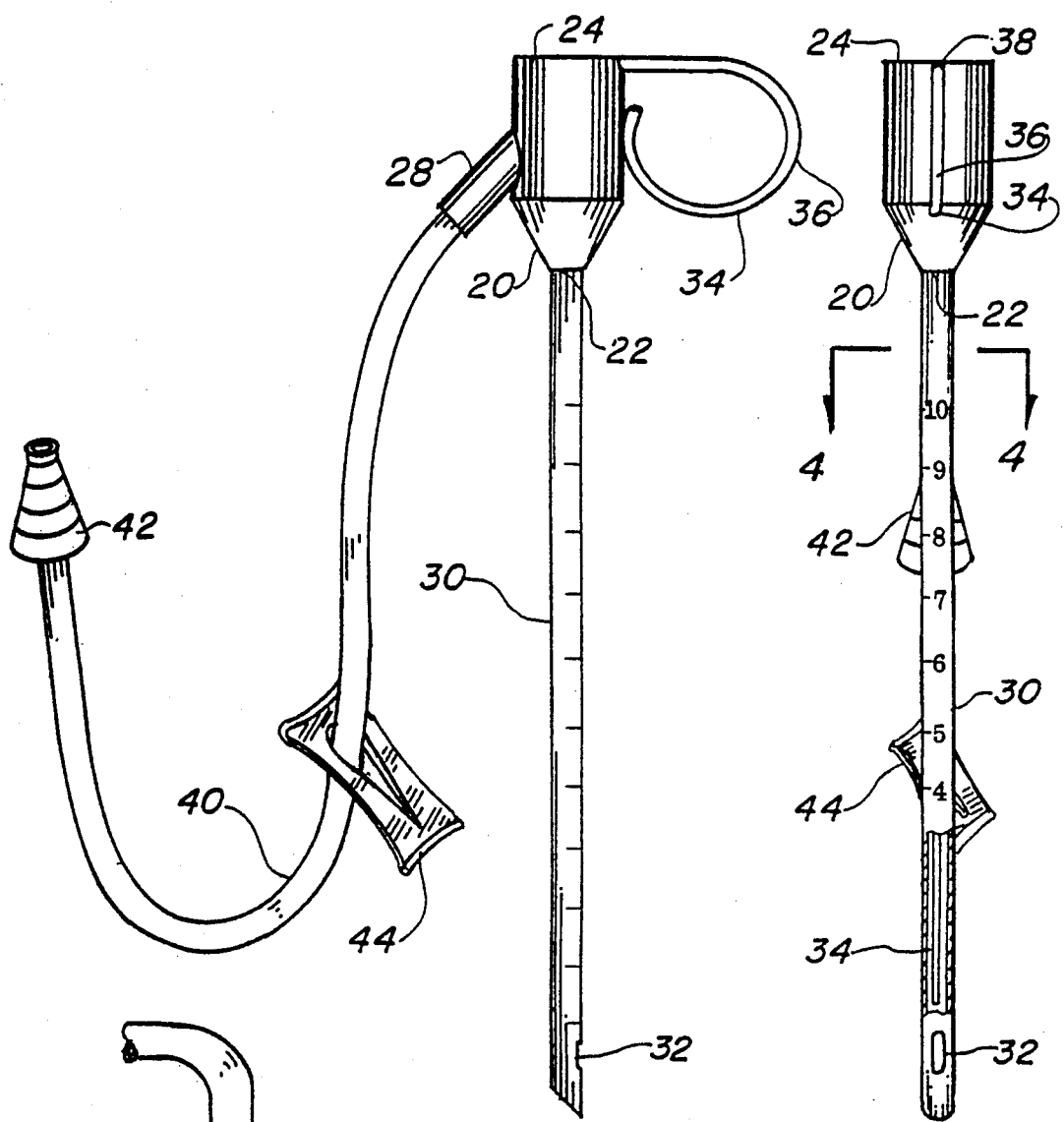
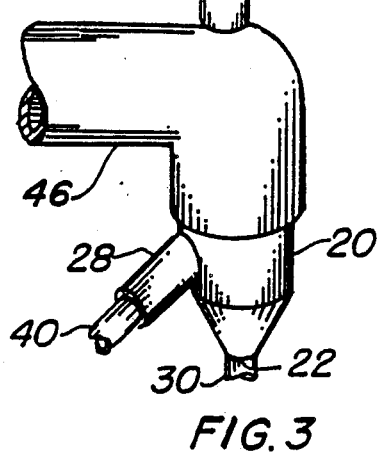
FIG. 1  FIG. 2
FIG. 3

MECONIUM ASPIRATION DEVICE

TECHNICAL FIELD

The present invention relates to aspirators in general, more particularly to hand regulated meconium aspirators for airway management of newborn infants.

BACKGROUND ART

Previously, many types of aspirators have been in use to provide an effective means for suctioning either from the medical practitioner providing the negative pressure by mouth or using mechanical suctioning equipment available in the clinical environment.

A search of the prior art did not disclose any patents that read directly on the claims of the instant invention, however, the following U.S. patents were considered related:

| U.S. Pat. No. | Inventor | Issue Date |
|---|---|---|
| 4,762,125 | Leiman et al | Aug. 9, 1988 |
| 4,369,991 | Linder | Jan. 25, 1983 |
| 4,248,236 | Linder | Feb. 3, 1981 |
| 4,275,724 | Behrstock | Jun. 30, 1981 |
| 4,185,639 | Linder | Jan. 29, 1980 |
| 4,033,331 | Guss et al | Jul. 5, 1977 |
| 3,957,055 | Linder et al | May 18, 1976 |
| 3,322,126 | Rusch et al | May 30, 1967 |

Leiman et al teach a balloon-tipped suction or extirpation catheter with an inflatable balloon mounted on and around the end of the catheter. The catheter further contains apertures above the balloon allowing suction or pressure to the area above the inflated balloon. A control port is disposed in the wall of the catheter for controlling transmission of suction forces.

Linder, in U.S. Pat. No. 4,248,236, teaches a catheter with a long, thin guide consisting of a polymer-coated wire of malleable material with the proximal end formed into a smooth handle.

Behrstock discloses an endotracheal intubation device having an inner flexible conduit and an outer shapable conduit slid over the top with suction applied by the medical practitioner. A suction trap is employed to prevent the meconium from being sucked into the users own mouth.

Guss et al invention is directed to a cardiac catheter having a catheter with a main lumen and a wire lumen. A wire is inserted, in a removable manner, into the wire lumen parallel with the main fluid lumen stiffening the catheter and allowing the creation of a plurality of different curvatures at the distal end to aid in obtaining visual representations of different areas of the cardiac system.

Rusch et al teach a surgically inserted tracheotoms catheter that allows a second catheter to be introduced into the first. An inflatable holder section surrounds the first on the outside to block the tracheal passage when inflated with a hand operated bulb. A support disc engages the outer portion of the patients neck with the second tube inserted into the first for removing fluids without interferring with the function of the first catheter.

Prior art known to be on the market includes a so-called "GESCO ASPIRATOR", registered trademark, manufactured by GESCO International of San Antonio, Texas, having a catheter, aspirator body with a thumb control port stopper, a hydrophobic fluid barrier and a suction line with an adapter.

Another device on the market is called a Meconium Aspirator and is produced by Intertech Resources, Inc., Bannockburn, Illinois. This aspirator includes a catheter, reservoir, filter, and a suction tube with a mouthpiece.

Finally, Hospital Concepts of Northridge, California produces an "HCI Meconium Aspirator" having a body with a thumb control port and adapter on one end for suction, also an adapter for a catheter on the other.

For background purposes and as indicative of the art to which the invention relates, reference may be made to the remaining cited patents.

DISCLOSURE OF THE INVENTION

The need to remove meconium from a newborn infant is well recognized in the medical profession as a variety of aspiration pneumonia may occur with term or part term infants who have passed meconium into the lungs. The most common method of meconium removal is tracheal suction under direct laryngoscopic vision soon after birth. An endotracheal tube, sometimes with a wire inside, is inserted and the wire removed. The medical practitioner places his or her mouth over the proximal end and sucks the meconium out. The procedure is repeated if all of the meconium is not retrieved, or if the tube is filled. The problems with this common procedure are obvious as the wire must be removed from the tube prior to suctioning which may inadvertently dislodge the tube and must be reinserted for reintubation. Further, since the mouth is on the tube, it is hard to visualize how full the tube is and the possibility of drawing the meconium into the mouth is very real which may cause cross-contamination by exposure to body fluids infected by AIDS, hepatitis, chlamydia, gonorrhea, herpes, syphillis, streptococcus, and the like.

It is, therefore, a primary object of the invention to provide a device that eliminates the need for mouth suctioning completely while utilizing the negative pressure that is already available in medical facilities. This is accomplished by providing a device that employs a chamber with an inlet, outlet, and a finger control port allowing the facility negative pressure, or suction, to be attached on the outlet and a catheter on the inlet. This invention then provides a suction pressure differential but is only used when needed by placing one's finger over the port. This allows constant or intermittent suction by the touch of the index finger in an easily controlled manner.

An important object of the invention further allows one hand operation of the deVice to both intubate and control the suction. The physical configuration of the aspirator is small enough to be easily held with one hand allowing a laryngoscope to be held in the other. This provides a clear unobstructed view of the pharynx area and the glottis, and suctioning may be accomplished without the necessity of laying down the light source to use both hands, nor does one's eyes have to be removed from the critical areas during the procedure.

Another object of the invention is directed to the angle of the outlet connection which is ideally at 45 degrees from the inlet. This arrangement allows the meconium that is in the suction tube to continue to travel down the tube by gravity and by entrained room air, even when the suction has stopped. This overcomes the problem that prior art has when mouth suctioning or even using similar aspirators that are on the market, as no provision is made to prevent the material remaining in the tube from dropping down into the infant's lungs by gravity when the suction is stopped.

Still another object of the invention allows a stylet to be used in conjunction with the catheter. While the use of stylets, or wires, in the lumen of the catheter may be well known and obviously advantageous, prior art has no method of manually controlling the suction if the stylet is in the catheter. The instant invention overcomes this problem by the use of a radial groove in the edge of the finger control port that snaps the stylet in place and still allows the port to be sealed by one's finger. The stylet may stay in place during the suctioning or may be removed at the choice of the person using the device.

Yet another object of the invention allows the flexibility for the aspirator to be used for ventilating if the infant becomes hypoxic after removal of the meconium has been completed. The preferred embodiment utilizes a standard 15 millimeter outside diameter endotracheal tube adapter for a finger control port. The stylet is removed and a conventional ventilating mechanism is attached over the port. An occlusion slide blocks the suction tube while the ventilating proceeds using well known techniques.

A further object of the invention allows the use of a catheter with markings to indicate the depth of penetration of the trachea. Further, the suction tube attaches to the standard hospital vacuum system with an universal type tubing connector for simple adaptation. If special adapters are required, the tubing is a standard size, normally 4 millimeter inside diameter, and may easily be connected to other configurations.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is a partial isometric view of the preferred embodiment.

FIG. 2 is a side view of the preferred embodiment, with the catheter partially cut-away to illustrate the stylet positioned inside.

FIG. 3 is a side view of the preferred embodiment with the stylet removed, the suction tube and catheter cut-away for clarity and the attaching portion of a ventilating device connected to the outside of the finger control port for the ventilating mode of operation.

BEST MODE FOR CARRYING OUT THE INVENTION

Figure 4:
FIG. 4 is a cross-sectional view taken along lines 4—4 of FIG. 2.
Figure 5:
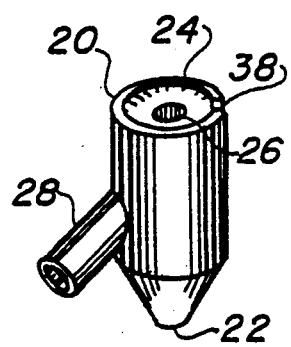
FIG. 5 is a partial isometric view of the aspirator body shown separately.
Figure 6:
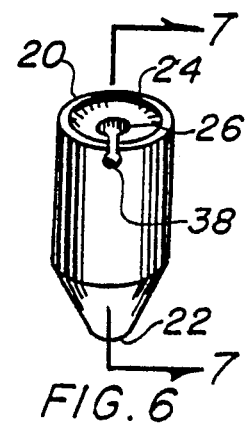
FIG. 6 is the same as FIG. 5, except rotated 90 degrees.
Figure 7:
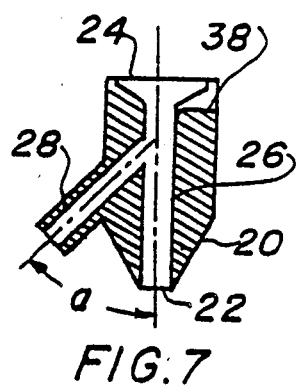
FIG. 7 is a cross-sectional view taken along lines 7—7 of FIG. 6.
Figure 8:
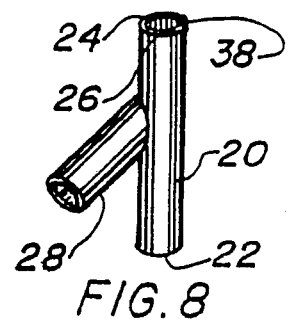
FIG. 8 is a partial isometric view of the cylindrical body in the thin tube configuration shown completely removed from the invention for clarity.
Figure 9:
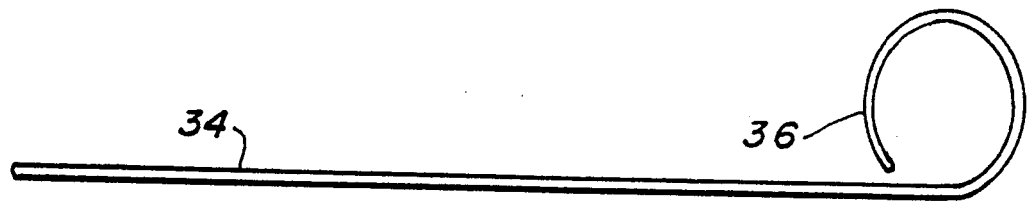
FIG. 9 is a side view of the stylet completely removed from the invention for clarity.

The best mode for carrying out the invention is presented in terms of a preferred embodiment. The preferred embodiment, as shown in FIGS. 1 through 9 is comprised of a cylindrical body 20 having a first and a second end and a hollow chamber inside. The body 20 has an inlet opening 22 on the first end and a finger control port 24 on the second end, both in communication with a hollow chamber 26 located within the body 20. An outlet passage 28, also contiguous with the chamber 26, is positioned on the side of the body 20 at an angular displacement from 30 to 60 degrees from the centerline of the inlet 22, with 45 degrees being preferred. The reason for this angular positioning is to allow meconium to flow down the outlet passage when the aspirating device is held vertical and suction, supplied through the outlet passage 28, is stopped and atmospheric pressure is present within the device. The body 20 is fabricated of any material such as metal, thermoset or the like with a thermoplastic material preferred. The body is injection molded with the finger control port 24 tapered inwardly, as shown in FIG. 7, so as to fit the contour of one's finger allowing a tight seal to be made when one's finger is placed over the port during use of the device. The physical size of the body may vary without affecting the aperture, however, a 15 millimeter outside diameter is preferred to interface with existing connectors in other uses. A variation of this size is illustrated in FIG. 8 wherein the diameter is only slightly larger than the attachments with the configuration functioning equally well with the exception of the standard outside diameter interface of the finger control port 24.

A suction catheter 30, preferably 2.5 to 3.5 millimeter inside diameter with a single lumen and indica imprinted thereon indicating the distance from the distal to the proximal end is attached to the inlet opening 22 of the body 20. The catheter 30 may also have a slot 32 near the distal end and the end is cut angularly. This catheter 30 by itself is well known in the art and commercially available. The length of the catheter 30 is sufficient to allow endotracheal intubation of an infant.

A stylet 34 looped into a handle 36 on one end made of a wire substantially uniform in diameter having sufficient flexibility to be bent by hand and covered with a polymer material is positioned within the device to preshape the catheter 30 easing the intubation process. The stylet 34 enters the finger control port 24, travels through the chamber 26 and inlet opening 22 and is disposed within the catheter 30 almost to the end just short of the slot 32. The handle portion 36 is fit into an inverted keyhole shaped radial groove 38 in the finger control port 24 in a snap-acting manner as the narrow part of the groove is smaller than the outside of the stylet 34. Further, this interface places the stylet 34 below the top surface of the port 24 allowing a seal to be made when one's finger is placed over the port, also removal is easy by simply pulling on the handle of the stylet 34.

A flexible suction link tube 40 is joined to the outlet passage 28 on one end and contains a connector 42 on the other. The connector 42 is well known in the art and is commercially available and has a slightly tapered end that fits most suction sources found in typical hospitals and delivery rooms. An occlusion slide 44 also common and available commercially is positioned over the suction link tube 40, as shown in FIG. 1, and functions to close off the tube by pinching into a tapered groove, or the like.

FIG. 3 illustrates a portion of a ventilation mechanism 46 that may be connected over the control port 24 with the stylet 34 removed. This procedure allows the aspiration device to be used to ventilate the lungs of a newborn infant while the catheter 30 is still inserted in the trachea. A ventilating mechanism of this type is well known in the art and requires only an interface connection to function properly. The most common size connector is 15 millimeters inside diameter, therefore, the body 20 and port 24 are sized accordingly, allowing this added function to increase the utility of the invention. The radial groove 38 in the port 24 presents no problem of air leakage, as it is completely covered by the connector of the ventilation mechanism 46.

In operation, the device is removed from its sterile package and the suction link tube 40 is connected to the hospital wall suction piping, or to a mechanical suction apparatus. The medical practitioner picks up a laryngoscope with one hand and places the lighted end in the newborn's mouth in the usual manner to visualize the pharynx and the vocal cords. The medical practitioner holds the meconium aspirator device in the other hand and places the distal end of the catheter 30 into the pharynx. If there is any meconium in the pharynx, it may be easily suctioned under direct vision by lightly touching the finger tip to the port 24. The trachea is then intubated without applying suction, rapid or intermittent suction may be applied, as required, visualizing the catheter all of the time. While intermittently applying suction under direct vision, the catheter 30 may be moved up and down the trachea without complete removal. This procedure may be repeated as many times as necessary in rapid succession until the meconium is completely removed and no fluid at all is visible. It is also possible to leave the stylet 34 in place or remove it at any point in the procedure permitting more flexibility in the catheter 30 and a larger area inside the lumen, if desired. Since there is no dead space from the end of the catheter 30 to the suction link tubing 40, gravity helps carry the meconium away from the infant even when suction is stopped. The entire process only takes a short period of time, as repeated intubation is unnecessary. Only one person is required to manage the entire procedure. When suctioning is completed, the stylet 34 may be removed, the suction link tube 40 pinched off by the occlusion slide 44 and a ventilating mechanism 46 attached to the finger control port 24 and the invention may then be used to ventilate using the well known techniques, as with a conventional endotracheal tube.

While the invention has been described in complete detail and pictorially shown in the accompanying drawings, it is not to be limited to such details, since many changes and modifications may be in the invention without departing from the spirit and the scope thereof. Hence, it is described to cover any and all modifications and forms which may come within the language and scope of the appended claims.

I claim:

1. A meconium aspiration device for airway management of newborn infants comprising:
   (a) a cylindrical body having first and second ends, and a side forming a hollow chamber therein;
   (b) said body having an inlet opening in the first end, and a finger control port on the second end, both in communication with the hollow chamber of the body allowing interconnection therebetween;
   (c) said body further having an outlet passage, said outlet passage being positioned on said side at an angular displacement of from 30 to 60 degrees from said inlet opening in communication with said hollow chamber such that gravity will not allow meconium to flow from the outlet to the inlet when the aspiration device is held vertical and no pressure differential exists between atmosphere and the device;
   (d) a suction catheter having a proximal end and a distal end with the proximal end connected to the inlet opening on the first end of the body allowing endotracheal intubation of an infant;
   (e) a stylet, looped into a right angle handle on one end, positioned within the finger control port, body hollow chamber and suction catheter, with the handle protruding outside of the body for stiffening said catheter and allowing preshaping to adapt the catheter to any desired contour; and,
   (f) a flexible suction link tube joined to said outlet passage on one end and having attaching means on the other for joining the aspiration device to a source of negative air pressure allowing intubation of the catheter into the pharynx and trachea of a newborn and suctioning the area, thereby removing meconium through the aspiration device's interconnecting openings, passages and chamber, and, adjusting the amount of suction by placing a finger on the control port in a regulating manner.

2. The aspiration device as recited in claim 1 further comprising, said outlet passage having an angular displacement of 45 degrees.

3. The aspiration device as recited in claim 1 wherein said suction catheter further comprises indica imprinted on the outside thereof indicating distance allowing visual determination of the depth of the intubation, and said catheter having a slot in one side in close proximity to the distal end.

4. The aspiration device as recited in claim 1 wherein said stylet further comprises a wire of substantially uniform diameter having sufficient flexibility to be bent by hand in a desired shape, covered with a polymer material of sufficient resilience to accommodate the desired bending while maintaining the integrity of the union.

5. The aspiration device as recited in claim 1 wherein said suction link tube attaching means further comprises a standard sized connector having a slightly tapered end such that an airtight interface is created.

6. The aspiration device as recited in claim 1 further comprising an occlusion slide disposed over said suction link tube such that the tube may be obstructed preventing suction from being applied by an outside source.

7. A meconium aspiration device for airway management of newborn infants comprising:
   (a) a cylindrical body having first and second ends, and a side forming a hollow chamber therein;
   (b) said body having an inlet opening in the first end, and a finger control port on the second end, both in communication with the hollow chamber of the body allowing interconnection therebetween;
   (c) said body further having an outlet passage, said outlet passage being positioned on said side at an angular displacement of from 30 to 60 degrees from said inlet opening in communication with said hollow chamber such that gravity will not allow meconium to flow from the outlet to the inlet when the aspiration device is held vertical and no pressure differential exists between atmosphere and the device;

(d) a suction catheter having a proximal end and a distal end with the proximal end connected to the inlet opening on the first end of the body allowing endotracheal intubation of an infant;

(e) a stylet, looped into a handle on one end, positioned within the finger control port, body hollow chamber and suction catheter, with the handle protruding outside of the body for stiffening said catheter and allowing preshaping to adapt the catheter to any desired contour;

(f) a flexible suction link tube joined to said outlet passage on one end and having attaching means on the other for joining the aspiration device to a source of negative air pressure allowing intubation of the catheter into the pharynx and trachea of a newborn and suctioning the area, thereby removing meconium through the aspiration device's interconnecting openings, passages and chamber, and, adjusting the amount of suction by placing a finger on the control port in a regulating manner.

(g) an occlusion slide disposed over said suction link tube such that the tube may be obstructed preventing suction from being applied by an outside source, and (h) a ventilation mechanism affixed over said finger control port with the stylet removed and said occlusion slide obstructing the suction link tube creating a contradistinction allowing the aspiration device to ventilate the newborn while the catheter is still in place.

8. A meconium aspiration device for airway management of newborn infants comprising:

(a) a cylindrical body having first and second ends, and a side forming a hollow chamber therein;

(b) said body having an inlet opening in the first end, and a finger control port on the second end, both in communication with the hollow chamber of the body allowing interconnection therebetween; said finger control port having an inverted keyhole shaped radial groove with the radial portion the same size as a stylet and a narrow portion open completely through the port allowing a stylet to snap into place in the groove and be held in place and out of the way when a finger is placed on the control port, (c) said body further having an outlet passage, said outlet passage being positioned on said side at an angular displacement of from 30 to 60 degrees from said inlet opening in communication with said hollow chamber such that gravity will not allow meconium to flow from the outlet to the inlet when the aspiration device is held vertical and no pressure differential exists between atmosphere and the device;

(d) a suction catheter having a proximal end and a distal end with the proximal end connected to the inlet opening on the first end of the body allowing endotracheal intubation of an infant;

(e) a stylet, looped into a handle on one end, positioned within the finger control port, body hollow chamber and suction catheter, with the handle protruding outside of the body for stiffening said catheter and allowing preshaping to adapt the catheter to any desired contour; and (f) a flexible suction link tube joined to said outlet passage on one end and having attaching means on the other for joining the aspiration device to a source of negative air pressure allowing intubation of the catheter into the pharynx and trachea of a newborn and suctioning the area, thereby removing meconium through the aspiration device's interconnecting openings, passages and chamber, and, adjusting the amount of suction by placing a finger on the control port in a regulating manner.

* * * * *